FLOWERING CRABAPPLE TREE

Filed Aug. 8, 1973

United States Patent Office

Plant Pat. 3,644
Patented Nov. 5, 1974

3,644
FLOWERING CRABAPPLE TREE

Henry A. Ross, Strongsville, Ohio, assignor to Cole Nursery Company, Inc., Circleville, Ohio Filed Aug. 8, 1973, Ser. No. 386,555
Int. Cl. A01h *5/03*
U.S. Cl. Plt.—34 1 Claim The present invention or discovery relates to a new and distinct variety of ornamental crabapple tree originated by me, having in combination novel fruit, foliage, and habit of growth, and more particularly consists in a novel variety of Malus, GV–18, flowering crabapple, having unusual and distinctive characteristics.

My new flowering crabapple tree is a small tree of medium to rapid growth rate having a rounded, umbrella-like top, with a distinct pendulous habit, each branch arching in pattern. The branches are slender and flexible giving a soft textured appearance, and, in bloom, the tree bears a large number of small white flowers, with abundant flower clusters at substantially every node along the twig, giving a "cloud" cover to the tree. The tree regularly bears an abundance of small, lemon yellow to greenish yellow fruits. Because of the tree's unusual growth habit and comparatively small size at maturity and abundant flowers, this new and distinct variety of ornamental crabapple tree is particularly suited for use for general landscape and park planting.

The novel and distinctive features of this new variety are accordingly considered to be, in combination:

1. The multi-branched form of the tree with soft textured arching and pendulous branches and rounded umbrella-like top.
2. The abundance of small white flower clusters.
3. The attractively shaped leaves which are of medium texture and moderate olive green on the top side and moderate yellow green to strong yellow green on the under side.
4. The small, glossy, lemon yellow to greenish yellow fruits which are borne abundantly and prominently in clusters of two to five.
5. The relative ease of production of the trees.
6. The apparent resistance of the trees to serious diseases.

There is a large demand for small ornamental flowering trees for landscape planting, and flowering crabapple trees have been recognized over a long period of time as especially suitable for such purposes. The tree of the present invention is particularly desirable because it affords, in combination, a distinct pendulous habit, with rounded, umbrella-like top and arching branches, an abundance of attractive flowers during the blooming period, and an abundance of glossy lemon yellow to greenish yellow fruits. Because of its unusual growth habit and comparatively small size at maturity and abundant flowers, this cultivar is especially suited for general landscape and park planting.

My new flowering crabapple tree has been propagated asexually at Painesville and Circleville, Ohio, by budding and grafting, and the tree can be very readily propagated in this manner, perpetuating all of its original characteristics. The original parent specimen was a seedling grown by me at Gardenview Horticultural Park, Strongsville, Ohio, and such original parent specimen was discovered and selected by me in a large plantation of crabapple tree seedlings grown by me from seeds.

Referring now more particularly to the drawing.

Figure 1:
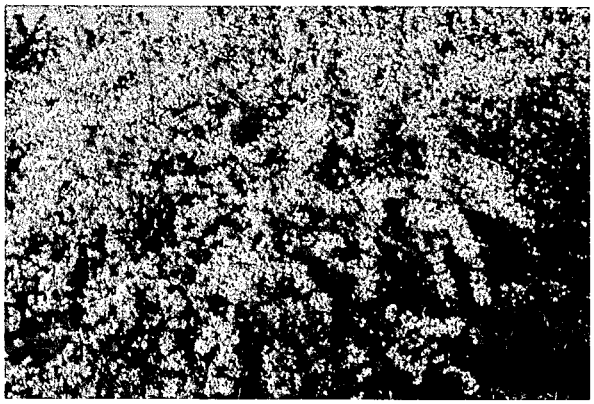
FIG. 1 shows my flowering crabapple tree in the spring blooming season.
Figure 3:
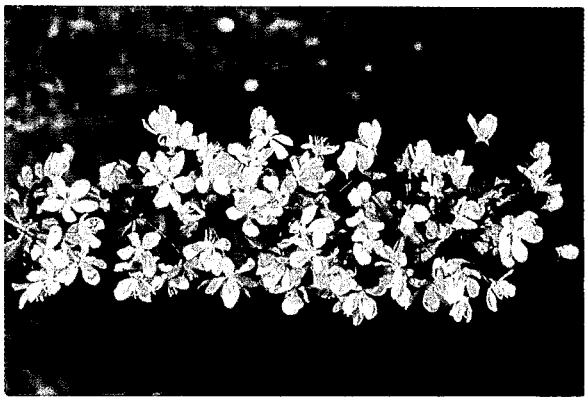
FIG. 3 shows a branchlet of such tree with such flowers in full and heavy bloom.
Figure 2:
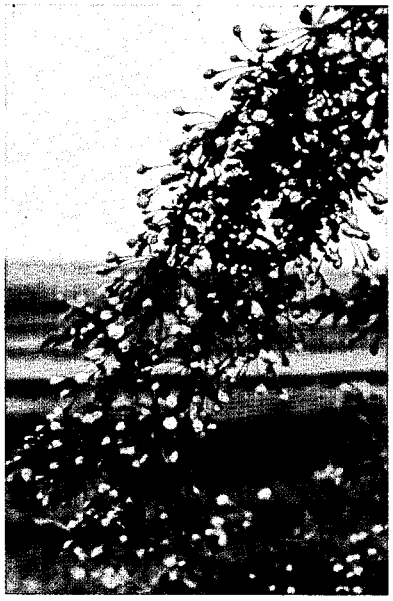
FIG. 2 shows a branchlet of such tree bearing a number of unopened flower buds.
Figure 4:
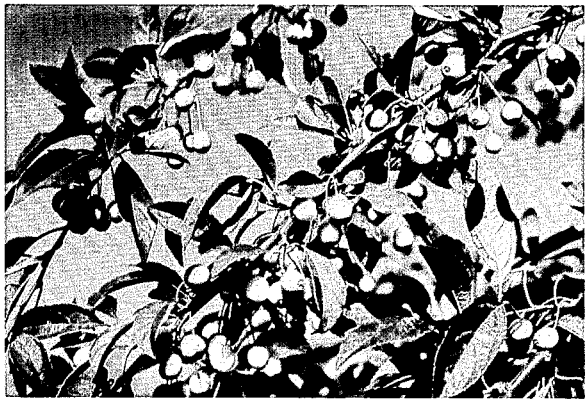
FIG. 4 shows the fruits and typical foliage of such tree, the fruit color having changed from yellow to brownish orange following a hard frost.

The following is a specific description of such new variety, the color terminology in reference to the buds, flowers, and foliage being based on the Nickerson Color Fan approved by the American Horticultural Society.

The original specimen is a tree approximately 15 feet high and 15 to 18 feet wide with a rounded, umbrella-like top and arching branches. The growth rate of this cultivar is medium to rapid, with a distinct pendulous habit, each branch arching in pattern. The inspected specimen propagated from the parent plant is approximately 8 feet high and 5 feet wide.

The branches of the tree are slender and flexible giving a soft textured appearance, and the branchlets are pubescent near the tip becoming nearly glabrous at the base of the current year's growth. Two-year branches are somewhat scurfy and essentially glabrous. The one-year twigs are moderate reddish brown to strong brown (7.5 R—3/6 to 2.5 YR—4/7) (Nickerson Color Fan), whereas the two-year twigs range from moderate olive brown to moderate yellowish brown (2.5 Y—4/4 to 10 YR—4/4). Lenticels are sparse and not prominent at the tips of the current season's growth, but become more plentiful and prominent near the base of one-year twigs, and are slightly raised and corky on two-year twigs.

The side, dormant, leaf buds are oblong, semi-pointed, mostly approximately 4–5 mm. in length, and are borne close or slightly diverging from the twig. The buds have 3 to 5 pairs of scales which are quite pubescent near the tip but less so near the base of one-year twigs. Bud color is moderate reddish brown (7.5 R—3/6), similar to the color of the one-year twigs.

The flower buds are ovid, approximately 10–12 mm. in length, and are strong purplish red to deep purplish pink (7.5 RP—5/12 to 7.5 RP—6/12). The color of the expanding flower buds is deep purplish pink to strong purplish pink (7.5 RP—6/12 to 7.5 RP—7/10).

The inner surface of the petals of the opening flowers is white tinged with light to strong purplish pink, whereas the color of the outer surface of the petals is a strong purplish pink to a light purplish pink (7.5 RP—7/10 to 7.5 RP—8/5). One day old flowers are essentially white but may have a pale purplish pink tint overcast which deepens around the margin of the petals.

The flowers are single, approximately 2.5 to 3.5 cm. across, composed of 5 petals, approximately 1.3 to 1.5 cm. in length, ovoid, with a short claw. The petals are somewhat variable, often with one of the five petals imperfect, and rounded at the tip with a wavy margin. The flower stems vary in length from approximately 3.3 to 4.2 cm., are flexible, somewhat curved and drooping. The pedicel color is variable, depending on exposure; varying from a moderate reddish brown to a deep purplish red (7.5 R—3/6 to 10 RP—3/10) where exposed to the sun, and are a dark greenish yellow (7.5 Y—6/7) where shaded.

Flower clusters are borne abundantly at substantially every node along the twig, giving a "cloud-like" cover to the tree, and there are usually 6 flowers per cluster although the number may vary from 4 to 6. Duration of bloom is approximately a week to ten days, flowering in late April or early May. The young developing leaves are essentially hidden by the abundance of flowers.

The leaves are generally elliptic to oblong in shape, very attractive, of medium texture, and moderate olive green (7.5 GY—4/4) above and moderate yellow green to strong yellow green (5 GY—5/6 to 5 GY—6/8) on the underside. The leaf blade is variable in size ranging from approximately 5.0 to 6.6 cm. in length, with a petiole of approximately 1.0 to 2.3 cm. on flowering shoots, to aproximately 6.0 to 9.0 cm. with a petiole of approximately 1.2 to 2.5 cm. in length on vegetative shoots. Leaves on two-year fruiting stems are quite variable, ranging from less than a centimeter in length to normal size.

The leaves are serrate to crenate-serrate, the teeth most prominent on leaves on vegetative shoots. Leaves on fruiting branches may be nearly entirely at the base. The veins of the leaf are anastomosing. The leaves are slightly hairy above, pubescent to sparingly pubescent below becoming essentially glabrous at maturity. The tips of the leaves are accuminate to short-accuminate, with leaf bases acute to tapering. Threadlike stipules are generally present early in the season but later wanting.

The fruits are small, glossy or sometimes russetted, aproximately 1.0 to 1.3 cm. long and 0.8 to 1.0 cm. broad at the widest point just below the middle, oblong in shape, borne abundantly and prominently in clusters of 2 to 5, mostly 4's. Final color of sun exposed fruit is lemon yellow to greenish yellow. The blush covers approximately one-third of the fruit surface. The color of shaded fruit is a strong greenish yellow (7.5 Y—7/9). The strongest color of the fruit is reached in late September to early October. The fruit stems are slender, drooping, tightly attached to the twigs and range in length from approximately 3.0 to 4.2 cm. The calyx is deciduous and both the stem and calyx ends of the fruit are depressed. The first hard frost changes the color of the fruit to an orange yellow which may be brownish orange to strong orange (5 YR—5/8 to 5 YR—6/11), and the fruit will remain on the tree after the first hard frost for many weeks until eaten by the birds.

Because of its unusual growth habit, comparatively small size at maturity, and abundant flowers, this cultivar is particularly suited for general landscape and park planting.

I claim:

1. A new and distinct variety of flowering crabapple tree, *Malus cultivar,* having a distinct pendulous habit, with rounded, umbrella-like top and arching branches, an abundance of small white flower clusters during the blooming period, and an abundance of small, glossy, lemon yellow to greenish yellow fruits.

No references cited.

ROBERT E. BAGWILL, Primary Examiner